United States Patent

Wang et al.

[11] Patent Number: 5,330,428
[45] Date of Patent: Jul. 19, 1994

[54] DILATATION CATHETER HAVING A RANDOM COPOLYMER BALLOON

[75] Inventors: Lixiao Wang, St. Paul; Bruce H. Rau, Clearwater; David Sogard, Edina, all of Minn.

[73] Assignee: SciMed Life Systems, Inc., Maple Grove, Minn.

[21] Appl. No.: 699,926

[22] Filed: May 14, 1991

[51] Int. Cl.$^5$ ............................ A61M 25/00
[52] U.S. Cl. ............................ 604/96; 604/264; 604/281
[58] Field of Search .......... 604/96–103, 604/280, 264, 281

[56] References Cited

U.S. PATENT DOCUMENTS

| | | |
|---|---|---|
| Re. 32,983 | 7/1989 | Levy ............................ 428/36.92 |
| Re. 33,561 | 3/1991 | Levy . |
| 2,995,779 | 8/1961 | Winter . |
| 3,088,173 | 5/1963 | Jones . |
| 3,141,912 | 7/1964 | Goldman et al. . |
| 3,432,591 | 3/1969 | Heffelfinger . |
| 3,627,579 | 12/1971 | Heffelfinger . |
| 3,733,309 | 5/1973 | Wyeth et al. . |
| 3,865,666 | 2/1975 | Shoney . |
| 3,908,201 | 9/1975 | Jones et al. ............................ 623/11 |
| 3,959,200 | 5/1976 | Scott ............................ 128/864 |
| 4,093,484 | 6/1978 | Harrison et al. . |
| 4,154,244 | 5/1979 | Becker et al. ............................ 128/349 |
| 4,254,774 | 3/1981 | Boretos . |
| 4,256,789 | 3/1981 | Suzuki et al. . |
| 4,367,747 | 1/1983 | Witzel . |
| 4,387,833 | 6/1983 | Venus, Jr. . |
| 4,411,055 | 10/1983 | Simpson et al. . |
| 4,413,989 | 11/1983 | Schjeldahl et al. . |
| 4,456,000 | 6/1984 | Schjeldahl et al. . |
| 4,490,421 | 12/1984 | Levy . |
| 4,531,943 | 7/1985 | Van Tassel et al. . |
| 4,531,997 | 7/1985 | Johnston . |
| 4,587,975 | 5/1986 | Salo et al. . |
| 4,608,984 | 9/1986 | Fogarty ............................ 128/344 |
| 4,637,396 | 1/1987 | Cook ............................ 128/344 |
| 4,646,742 | 3/1987 | Packard et al. . |
| 4,743,258 | 5/1988 | Ikada et al. ............................ 623/11 |
| 4,807,619 | 2/1989 | Dyrud et al. ............................ 128/206.16 |
| 4,884,573 | 12/1989 | Wijay et al. ............................ 128/344 |
| 4,906,244 | 3/1990 | Pinchuk et al. ............................ 606/194 |
| 4,938,676 | 7/1990 | Jackowski et al. ............................ 425/140 |
| 4,941,877 | 7/1990 | Montano, Jr. ............................ 604/96 |
| 4,950,239 | 8/1990 | Gahara et al. ............................ 604/96 |
| 4,952,357 | 8/1990 | Euteneuer ............................ 264/129 |
| 4,963,313 | 10/1990 | Noddin et al. ............................ 264/573 |
| 5,108,415 | 4/1992 | Pinchuk et al. ............................ 604/96 |
| 5,156,612 | 10/1992 | Pinchuk et al. . |
| 5,264,260 | 11/1993 | Saab ............................ 428/35.5 |

FOREIGN PATENT DOCUMENTS

| | | |
|---|---|---|
| 0135990 | 4/1985 | European Pat. Off. . |
| 0186267 | 7/1986 | European Pat. Off. . |
| 0274411 | 7/1988 | European Pat. Off. . |
| 0345051 | 12/1989 | European Pat. Off. . |
| 0355937 | 2/1990 | European Pat. Off. . |
| 0362826 | 4/1990 | European Pat. Off. . |
| 0492361A1 | 7/1992 | European Pat. Off. . |
| WO89/08473 | 9/1989 | PCT Int'l Appl. . |
| WO92/08512 | 5/1992 | PCT Int'l Appl. . |

OTHER PUBLICATIONS

Hsiue, Ging-Ho et al. "Thermal Shrinkage at the drawing poly(ethylene isophthalate ferephtholate) copolyester films", E. I. Monthly EI8907064651 *Journal of Applied Polymer Science* vol. 37 No. 10 May 20, 1989 pp. 2803–2816 (abstract only).

Kahn et al., *Catherization and Cardiovascular Diagnosis*, 21:144–147 (1990).

Dupont Industry News, Du Pont Company/Marketing Communications Department/ Wilmington, DE 19898.

(List continued on next page.)

*Primary Examiner*—C. Fred Rosenbaum
*Assistant Examiner*—Chalin Smith
*Attorney, Agent, or Firm*—Vidas, Arrett & Steinkraus

[57] ABSTRACT

The present invention provides a dilatation catheter which includes a balloon having at least one layer of a thermoplastic material consisting essentially of a random copolymer made from dimethyl terephthalate dimethyl isophthalate and ethylene glycol. These balloons are particular suited for use on dilatation catheters used for percutaneous transluminal coronary angioplasty.

22 Claims, 1 Drawing Sheet

OTHER PUBLICATIONS

P. Chandran and S. A. Jabarin, "Biaxial orientation of Poly(Ethylene Terephthalate)," pp. 880–885, *Antec '91*.

P. Tugcu, K. W. Neale and A. Marquez-Lucero, "Effect of Deformation-Induced Heating on the Cold Drawing of Polymeric Films," pp. 104–111, Jan. 1991, *Journal of Engineering Materials and Technology*.

M. Cakmak, Y. D. Wang, and M. Simhambhatla, "Processing Characteristics, Structure Development, and Properties of Uni and Biaxially Stretched Poly(Ethylene 2,6 Naphthalate) (PEN) Films," pp. 721–733, Jun. 1990, *Polymer Engineering and Science*, vol. 30, No. 12.

S. A. Jabarin, "Crystallization Behavior of Poly(Ethylene Terephthalate)," pp. 1259–1264, Sep. 1989, *Polymer Engineering and Science*, vol. 29, No. 18.

Jiayu Guan, Wei Wu, Xiaoli Zhang, Zimian Ma & Mao Xu, "Influence of Molecular Weight on the Tensile Behaviour of PET Films Under Biaxial Stretching," pp. 23–27, 1989, *Plastics and Rubber Processing and Applications*, vol. 11, No. 1.

"CLEARTUF 7207," The Goodyear Tire & Rubber Company, (Advertisement), 1989.

Schneider Shiley, "Presenting An Inflated View of A Systematic Approach to Peripheral Angioplasty," (Advertisement), Nov. 1987.

S. A. Jabarin, "Crystallization Kinetics of Polyethylene Terephthalate I. Isothermal Crystallization From the Melt," pp. 85–96, 1987, *Journal of Applied Polymer Science*, vol. 34.

M. F. Vallat and D. J. Plazek, "Effects of Thermal Treatment of Biaxially Oriented Poly(Ethylene Terephthalate)," pp. 2123–2134, 1986, *Journal of Polymer Science: Part B: Polymer Physics*, vol. 24.

Frank P. Leigner, "Free-blown PET preforms characterize blown bottles," pp. 47–51, Jun. 1985, *Plastics Engineering*.

Frank P. Leigner, "Freeblowing PET Preforms," pp. 907–915, 1985, *ANTEC '85*.

R. T. Bailey, F. R. Cruickshank, A. McLeod, D. Pugh and A. G. Faraday, "Thermal lens measurements of thermal conductivity and orientation in polyethylene terephalate," pp. 23–25, Jan. 1985, *Polymer Communications*, vol. 26.

Takaka Terada, Chie Sawatari, Toyoko Chigono and Masaru Matsuo, "Oriented Crystallization of Poly(ethylene terephthalate) under Uniaxial Stretching," 1982, *American Chemical Society*.

G. S. Kirshenbaum and J. M. Rhodes, "Thermoplastic polyester: PET," pp. 50–51, 1981–1982, *Modern Plastics Encyclopedia*.

C. Bonnebat, G. Roullet and A. J. deVries, "Biaxially Oriented Poly(Ethylene Terephthalate) Bottles: Effects of Resin Molecular Weight on Parison Stretching Behavior," pp. 189–195, Mar. 1981, *Polymer Engineering and Science*, vol. 21, No. 4.

G. Hinrichsen, A. Eberhardt, U. Lippe, and H. Springer, "Orientation mechanisms during biaxial drawing of polymer films," pp. 73–79, 1981, *Colloid & Polymer Science*, vol. 259, No. 1.

B. J. Jungnickel, "Analysis of the Degree of Orientation of Biaxially Drawn Polyethylene Terephthalate Foils," 1980, *Progr. Colloid Polym. Sci.*, 67, 159–160, (3 page translation).

Bruce F. Blumentritt, "Anisotropy and Dimensional Stability of Biaxially Oriented Poly(ethylene Terephthalate) Films", pp. 3205–3217, 1979, *Journal of Applied Polymer Science*, vol. 23.

R. B. Fredrickson, "Stretch-Blow Molding for Packaging Versatility," pp. 22–26, Nov. 1979, *Plastics Design & Processing*.

Andreas R. Grotzig, Ake Senning, and Walter E. Siegenthaler, "Nonoperative Dilation of Coronary-Artery," pp. 61–68, Jul. 12, 1979, *The New England Journal of Medicine*, vol. 301, No. 2.

C. Shriver, "How to Reheat Blow Mold PET Soft Drink Bottles," pp. 91–93, Oct. 1977 (journal unknown).

Daniel D. Ray, Clem B. Shriver and Robert J. Gartland, "Here's Why Polyethylene Terephthalate Is the Major Competitor For Beverage Container Applications," pp. 47–50, Sep. 1977, *Plastics Design & Processing*.

Raymond B. Seymour, "The Narrowing Field of Plastics For Blow Molded Beverage Containers," pp. 61–65, Jun. 1977, *Plastics Design & Processing*.

D. V. Rosato, "Processing PET," pp. 545–553, *Polyethylene Terephthalate (PET)* (date unknown).

Yoshinori Nakamura, "PET stretch-blowing-Application Development and Improvement of Product Quality," pp. 14–22, *Japan Plastics Age* (date unknown).

Saleh A. Jabarin and Elizabeth A. Lofgren, "Effects of Water Absorption on Physical Properties and Degree of Molecular Orientation of Poly(Ethylene Terephthalate," 6 pages (date and journal unknown).

P. R. Ajmera and N. R. Schott, "Elevated Temperature Tensile Properties of Biaxially Oriented PET and PET/PETG Blends," pp. 710–712 (date and journal unknown).

DILATATION CATHETER HAVING A RANDOM COPOLYMER BALLOON

The present invention generally relates to a dilatation catheter fitted with an inflatable balloon which expands against the internal walls of a vessel to open or dilate a constriction, stenois or occlusion-of the vessel and, particularly, relates to a dilatation catheter for use in percutaneous transluminal coronary angioplasty.

BACKGROUND OF THE INVENTION

Percutaneous transluminal coronary angioplasty (PTCA) is an efficient and effective procedure for treating vascular disease caused by or associated with stenosis of coronary arteries. Typically, a physician fluoroscopically guides a catheter fitted with an expandable balloon, from an entry point at the femoral artery, through a patient's arterial system to the site of the stenoisis or occlusion. The expandable balloon of the catheter is then positioned across the stenosis or occlusion and the balloon is inflated with fluid to dilate the artery and open the obstructed passageway. The dilated artery reestablishes an acceptable blood flow through the artery without resorting to more serious, invasive surgical procedures such as grafts or by-passes.

The PTCA procedure places unique demands on the types of materials needed to fabricate a catheter fitted with an expandable balloon. The physical properties and characteristics of a desirable balloon may result in certain characteristics being balanced against others. For example, a minimum balloon profile is advantageous because it allows the balloon to easily reach and then traverse tight stenosis or occlusions with minimum trauma to arterial vessels. A minimum balloon profile may be achieved by minimizing the wall thickness of the balloon material but thinner walls of the balloon material gives a weaker balloon (compared to a thicker wall) and thus reduces the amount of pressure that can safely be used to inflate the balloon and open a stenosis.

Similarly, very strong thermoplastic materials that are sufficiently strong enough to allow for minimum balloon wall thicknesses tend to be rigid, hard or stiff compared to more elastomeric materials that tend to be flexible, soft and deformable. Using stronger materials may give a minimum profile balloon but the stiffness of the material may be more likely to injure or traumatize the vascular system as the balloon is positioned to and then across a stenosis or occlusion.

In the past, PTCA catheter balloons have been made from polymeric materials which gave balloons that may be broadly categorized into two groups: a) non-distensible balloons and b) distensible balloons. Non-distensible balloons typically inflate to a nominal diameter and then do not significantly stretch or expand beyond that diameter as the pressure is increased. These types of balloons are not stretchable or compliant. See, for example, U.S. Pat. No. 32,983 to Levy which describes a biaxially oriented, polyethylene terephthalate homopolymer (PET) balloon. In comparison, distensible balloons typically inflate to a nominal diameter and then continue to stretch or expand as the inflation pressure is increased until the strength of the balloon material is exceeded and the balloon bursts. Polyvinyl chloride, polyethylenes and homopolymers or copolymers of olefins have been used to make distensible balloons. See, for example, U.S. Pat. No. 4,154,244 to Becker et al. which describes a thermoplastic rubber balloon.

Distensible balloon materials such as polyvinyl chlorides and polyethylenes characteristically have lower tensile strengths compared to non-distensible balloon materials such as PET or polyimides. The comparatively lower tensile strength of distensible balloon may increase the risk of possible balloon failure if the balloon is over inflated.

Distensible balloons having high expansion properties also present the risk that a blood vessel may be damaged or ruptured due to uncontrolled overinflation. Even so, the relatively high expansion properties of distensible balloons compared to non-distensible balloons provides some advantages. The distensible balloon gives the physician some margin of error in matching a specifically sized balloon with the size of the vessel at the stenosis site. At least in theory, the physician will select a balloon which has the same inflated diameter as the finally dilated artery. In practice; however, assessment of the artery's size can be miscalculated and the greater expansion of a distensible balloon allows the physician to obtain a correct dilatation diameter by using higher inflation pressures (provided, of course, that the balloon material may handle such higher pressures).

Non-distensible balloon materials characteristically have much higher tensile strengths than distensible balloon materials. The higher tensile strengths of non-distensible balloon materials are generally a result of orienting the balloon material during manufacture of the balloon. The orientation process unavoidably imparts stresses and varying degrees of crystallinity or nonhomogeneity in the balloon material which, if ignored, gives an undesirable balloon. PET is a sensitive, unforgiving material when it is processed. During the stretch blow molding process typically used to form PET balloons, the risk exists that thin walled PET balloons will have nonhomogeneous regions in the balloon wall. This nonhomogeneity may result in the formation of pinholes and other weakening of the wall which can lead to balloon failure when it is inflated under pressure. Pinholes are particularly disadvantageous because if the pinhole forms when the balloons is under elevated pressure, a high velocity jet of inflation fluid may be emitted which can cause arterial dissection. The nonhomogeneity of PET materials may be compensated for by using thicker balloon walls but thicker walls may not be preferred. Further, PET balloon have been found to be quite fragile and may be easily damaged during routine handling. The non-distensible properties of PET balloon also require that a physician has to withdraw and replace a balloon which proves to be smaller than needed to fully dilate the artery. Finally, PET balloons have been found to develop extensive wrinkles when the balloon is sterilized. These undesired wrinkles may inhibit the easy advancement of the catheter through the arterial system.

Furthermore, PET balloon materials do not readily take a fold or a crease. As such when these balloons are collapsed in a deflated state the collapsed balloon flattens and provides an undesired "winged" profile. The phenomenon of "winging" results when the flat, lateral portions of the deflated balloon project laterally outward beyond the rest of the catheter. A "winged" balloon presents a profile having rigid edges which has a much higher likelihood of injuring the arterial system during placement of the balloon.

In addition to PET, other types of materials have been used to produce non-distensible balloons are reported. See, for example, U.S. Pat. Nos. 4,938,676 and 4,906,244 that report using a biaxially oriented nylon or polyamide material, U.S. Pat. Nos. 4,884,573 and 4,952,357 that report using a polyimide material and U.S. Pat. No. 4,950,239 that reports using a polyurethane material.

In spite of extensive ongoing efforts to produce an "ultimate" catheter balloon, no single material has been found to be overwhelmingly satisfactory for balloons needed to perform PTCA.

There is clearly a continuing need in this field for a catheter balloon made from a polymer material having properties which are optimized for PTCA.

SUMMARY OF THE INVENTION

This invention provides a dilatation catheter having a compliant balloon that includes at least one layer of a thermoplastic material of a random copolymer made from dimethyl terephthalate dimethyl isophthalate and ethylene glycol. The structure of the copolymer includes random repeating units of ethylene terephthalate and ethylene isophthalate as illustrated in Formula 1.

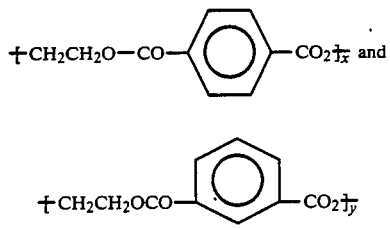

Formula 1

This material may be used to produce a balloon that is substantially compliant and essentially deformable when the catheter is placed in the arterial system of a patient.

Preferable, the random copolymer has a ratio of ethylene terephthalate units (x) to ethylene isophthalate units (y) of between 99:1 to 80:20 and more preferably the ratio is about 95:5 to 90:10 and a particularly preferred ratio is about 92:8.

Catheter balloons made of the present random copolymer preferably have an intrinsic viscosity less than 0.8 dl/g., a tensile strength less than 40,000 psi a radial expansion greater than 3% at 200 psi and great than 7% burst when the radial expansion in measured at 37° C. Balloons made of a random copolymer and having a radial expansion greater than 5% at 200 psi and greater than 10% at burst and a tensile strength less than 31,000 psi are also within the scope of this invention.

The use of the present random copolymer in a dilatation catheter balloon of this invention allows the wall thickness of the balloon to be about 0.0076–0.051 mm. In addition, the random copolymer layer is more amorphous and less crystalline than a biaxially oriented polyethylene terephthalate homopolymer balloon having a tensile strength greater than 31,000 psi.

Advantageously, the present random copolymer also is easier to extrude into tubing which is then stretched and molded into balloons as compared to PET. These properties allow the production of balloons having greater uniformity and higher quality then balloons made of other materials and as such provide important benefits in overall quality and reliability to the physicians and patients performing or undergoing PTCA.

DETAILED DESCRIPTION

Figure 1:
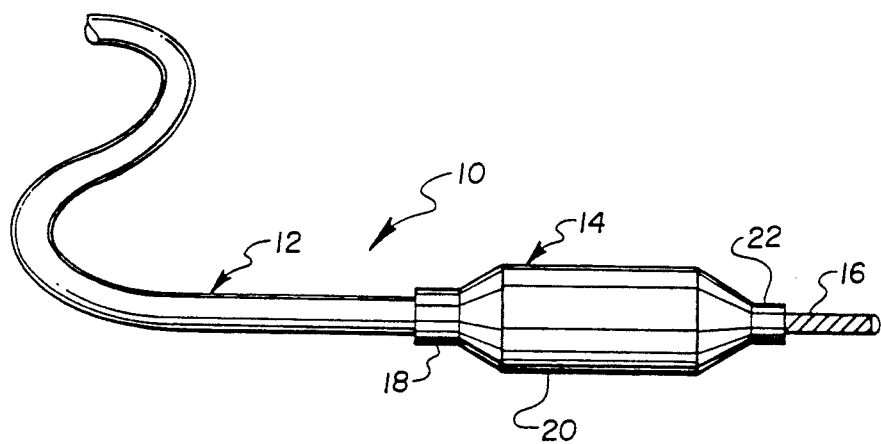
FIG. 1 is a perspective view of a balloon catheter having a balloon made of a random copolymer material.

FIG. 1 illustrates a typical dilatation balloon catheter (10) which has an elongated flexible shaft (12) with inflatable balloon (14) fitted at its distal end. In FIG. 1, a balloon (14) is shown in its fully inflated condition. Extending out the distal end of balloon (14) is flexible distal tip (16). Depending upon the particular construction of catheter (10) the tip (16) may be the distal end of a movable guidewire which extends through shaft (12) and balloon (14,) or may be the distal end of a fixed wire or core which is bonded to balloon (14).

The flexible shaft (12), which is preferably a polymeric tube, has at least one lumen extending from its proximal to its distal end. Depending upon the particular construction of the catheter (10), multiple lumens may be provided in shaft (12). In any case, at least an inflation lumen extends through shaft (12) for selective inflation and deflation of balloon (14) using a suitable fluid.

Balloon (14) is preferably a thin walled balloon which has a proximal waist portion (18) fitted or attached to the distal end of shaft (12), an intermediate inflatable balloon section (20) and a distal end section (22.) Assembly of the various components of the catheter (10) is readily accomplished using established procedures and techniques.

The random copolymer used to make a catheter balloon of the present invention is prepared according to standard procedures from ethylene glycol, and a mixture of dimethyl terephthalate and dimethyl isophthalate. As used in the random copolymer, the ratio of terephthalate to isophthalate in the random copolymer may be varied over the range of between 99:1 to 80:20. It should be understood that slight differences in the ratio of the two phthalates will provide random copolymers with different physical properties and characteristics. Some of these random copolymers may be commercially available and are sold under the tradename Selar ® PT by E. I. Dupont de Nemours and Company, Wilmington, Del. The comparative physical properties of several random copolymers which may by used in the present invention and PET are listed in Table I.

TABLE I

| Physical | Copolyesters | | | |
|---|---|---|---|---|
| Properties | I | II | III | PET |
| Ratio of terephthalate to isophthalate[(1)] | 97/3 | 92/8 | 87/13 | 100/0 |
| IV g/dl[(2)] | 0.80 | 0.80 | 0.68 | 1.02 |
| Melting T °C.[(2)] | 245 | 230 | 221 | 254 |
| Recrys. T °C.[(3)] | 140 | 143 | 149 | 133 |
| Crystallinity %[(3)] | 23 | 18 | 15 | 30 |
| Glass Temp. °C.[(3)] | 77 | 76 | 74 | 77 |

[(1)]The ratio of terephthalate (x) to isophthalate (y) is determined by proton NMR at 499.834 MHz using acquisition times of more than one hour.
[(2)]Intrinsic viscosity (IV) and melting temperature data were provided by the manufacturer, DuPont.
[(3)]Recrystallization temperature was measured by differential scanning calorimetry and crystallinity was estimated from virgin resin pellets.

It is noted that small subtle changes in the given ratio of the phthalates in the random copolymer may provide materials having different physical characteristics.

The production of catheter balloons made from the random copolymers listed above begins by initially extruding the material into tubing according to the following method.

TUBING EXTRUSION

In order to prepare balloons made of the present random copolymers the thermoplastic material is initially extruded into tubing according to the following method. A selected random copolymer is dried by a desiccant hot air dryer using −40° F. dew point air in a plenum style hopper. Polymer moisture content is controlled within a range of 10 to 70 ppm by varying drying temperature and time. The extruder is a specially configured laboratory model with a high torque drive system such as the extruder, PL 2000, sold by C. W. Brabender, manufactured in W. Germany and assembled in S. Hackensack, N.J. The extruder length to diameter ratio is about 20:1 with a minimum of three temperature control zones and additional heater zones for adapter, head and die. Temperature controllers are of the proportioning type in order to maintain tight temperature control and a homogeneous melt. Both barrel and screw of the extruder are made of conventional bimetallic material that is surface hardened and chrome plated. A preferred screw for the extruder is a barrier flight screw which gives improved melt uniformity and mixing without excessive shear or polymer degradation; however, a general purpose screw with a 3:1 compression ratio and a relatively constant transition from feed to metering zone also works effectively. Breaker plate, adapter, head and tooling are streamlined, i.e., gradual transitions, rounded edges and minimal obstructions. Screen packs of 60-80-60 mesh are generally sufficient to generate adequate back pressure. Die and tip drawdown ratios are maintained between 2:1 and 3:1, and die land lengths are about 10 to 20 times the desired tubing wall thickness. Sizing is accomplished by free extrusion and maintaining constant nitrogen pressure inside the tubing while being quenched in a conventional water bath at ambient temperatures. Specific extrusion parameters used to extrude the random copolymers into appropriately sized tubing are listed in Table II.

Table II also lists PET for comparative purposes. The lower extrusion temperatures listed in Table II for the random copolymers demonstrate the random copolymers compared to PET allows the extrusion process to be less complex and easier to control. As such the extruded tubing made from the random copolymers possesses more controlled dimensional tolerances and concentricity.

The extruded tubing is formed into balloons according to the following method.

BALLOON FORMATION

Some initial orientation of the random copolymers is accomplished as the material is drawn down during extrusion. This process is typically known as machine orientation and is in the direction of extrusion operation. It is important that machine orientation be controlled to minimize orientation during extrusion. Principle orientation in the machine direction is achieved by heating and physically stretching the extruded random copolymer tube in the machine direction during balloon formation. This results in principle orientation and reduces the cross-sectional area of the tubing. The temperature for this heating and stretching operation ranges form 80–99° C., but is more preferably performed at between 86–97° C. Preferred stretching conditions for random copolymer tubing having a finite length (L) and an inner diameter (ID), is a length ($L_2$) which is greater than L but less than 3L. In general, lower stretching ratios and lower heating temperatures result in a more compliant balloon.

After the copolymer tubing is oriented in the machine direction it is then oriented in a transverse direction using a blow molding technique. Briefly, a pressurized gas is applied to the inside of the tubing that is heated to temperatures of from 80–99° C. The tubing is expanded in a mold to a diameter which is less than 6.5 times its initial inside diameter and then cooled to room temperature. The blowing pressure and stretching ratio in this transverse direction have a controlling effect on final balloon wall thickness. Lower transverse expansion, temperatures and pressures result in substantially compliant balloons. Preferably, balloons produced by this method have a radial expansion of more than 3% at 200 psi and more than 7% at burst for body temperatures of 37° C., and a wall tensile strength from 15,000 to 40,000 psi for a wall thickness of 0.0076 mm to 0.051 mm. Balloons formed from a preferred random copolymer have an intrinsic viscosity less than 0.8 dl/g.

EXAMPLE

Following the processes described above, catheter balloons of various sizes were made from the random copolymers listed in Table I. The important manufacture parameters and physical characteristics of the balloons are listed in Table III.

TABLE II

| Random Copolymer | EXTRUSION CONDITIONS[1] | | | | | | Melting | |
|---|---|---|---|---|---|---|---|---|
| | Temperature °C. | | | | | | | |
| | Zone 1 | Zone 2 | Zone 3 | Zone 4 | Zone 5 | Zone 6 | Pressure | Temperature |
| I | 248 | 249 | 249 | 249 | 248 | 265 | 4100 psi | 258° C. |
| II | 244 | 243 | 243 | 244 | 244 | 257 | 6600 psi | 254° C. |
| III | 229 | 232 | 233 | 233 | 227 | 230 | 4800 psi | 242° C. |
| PET | 275 | 272 | 267 | 259 | 258 | 275 | 2900 psi | 272° C. |

[1]The temperature and melting pressure vary slightly for both the different tubing sizes and the molecular weight of the feedstock.

TABLE III

| Copolymers | II | II | II | II | II | II | III | III | III |
|---|---|---|---|---|---|---|---|---|---|
| Tube OD[1] (mm) | .6350 | .7874 | .6350 | .7874 | .6350 | .7874 | .8382 | .8382 | .8382 |
| Tube ID[2] (mm) | .4064 | .5334 | .4064 | .5334 | .4064 | .5334 | .4572 | .4572 | .4572 |
| Axial Stretching Ratio[3] | 1.5 | 1.5 | 2.0 | 2.0 | 2.5 | 2.5 | 2.0 | 2.2 | 2.4 |
| Axial Stretching Temp. °C. | 95 | 95 | 95 | 95 | 95 | 95 | 95 | 95 | 95 |

TABLE III-continued

|  | | | | | | | | | |
|---|---|---|---|---|---|---|---|---|---|
| Balloon Diameter (mm) | 2.15 | 2.93 | 2.14 | 2.93 | 2.15 | 2.94 | 2.72 | 2.72 | 2.72 |
| Balloon Thickness (mm) | .0133 | .0165 | .0140 | .0146 | .0133 | .0133 | .0160 | .0152 | .0154 |
| Blowing Temp. °C. | 95 | 95 | 95 | 95 | 95 | 95 | 95 | 95 | 95 |
| Expansion Ratio[4] | 5.2 | 5.4 | 5.2 | 5.4 | 5.2 | 5.5 | 5.88 | 5.88 | 5.88 |
| Burst Pressure psi | 300 | 280 | 320 | 290 | 300 | 280 | 243 | 255 | 263 |
| Wall Tensile Strength psi | 24184 | 24845 | 24509 | 29089 | 24184 | 30866 | 20652 | 22755 | 23085 |
| Radial Expansion at 200 psi | 7.5% | 8.2% | 6.5% | 6.1% | 7.9% | 8.5% | 10% | 7.0% | 6.0% |
| Radial Expansion at Burst | 19% | 26% | 17% | 19% | 23% | 24% | 18% | 13% | 13% |
| Copolymers | III | I | II | II | II | I | I | I | III |
| Tube OD[1] (mm) | .8382 | .9144 | .9652 | .7722 | .6414 | .9144 | .9144 | .9144 | .8382 |
| Tube ID[2] (mm) | .4572 | .6096 | .6096 | .5131 | .4128 | .6096 | .6096 | .6096 | .4572 |
| Axial Stretching Ratio[3] | 2.5 | 2.0 | 2.25 | 2.0 | 2.0 | 2.0 | 2.0 | 2.0 | 2.6 |
| Axial Stretching Temp. °C. | 95 | 90 | 95 | 90 | 90 | 90 | 90 | 90 | 95 |
| Balloon Diameter (mm) | 2.72 | 3.18 | 3.43 | 2.97 | 2.46 | 2.71 | 2.95 | 3.44 | 2.73 |
| Balloon Thickness (mm) | .0156 | .0140 | .01524 | .0127 | .0114 | .0197 | .0159 | .0114 | .0165 |
| Blowing Temp. °C. | 95 | 90 | 95 | 90 | 90 | 90 | 90 | 90 | 95 |
| Expansion Ratio[4] | 5.88 | 5.17 | 5.58 | 5.74 | 5.90 | 4.38 | 4.78 | 5.60 | 5.90 |
| Burst Pressure psi | 270 | 260 | 290 | 280 | 280 | 300 | 280 | 260 | 300 |
| Wall Tensile Strength psi | 23507 | 29591 | 32635 | 32740 | 30211 | 20634 | 25975 | 39228 | 24818 |
| Radial Expansion at 200 psi | 6.0% | 7.8% | 4.0% | 4.0% | 4.8% | 4.4% | 5.1% | 5.8% | 4.0% |
| Radial Expansion at Burst | 16% | 20% | 12% | 10% | 12% | 11% | 15% | 14% | 8.8% |

[1]OD = outsider diameter.
[2]ID = inner diameter.
[3]Axial stretching ratio is the ratio of stretched length to initial length before axial stretching.
[4]Expansion ratio is the ratio of balloon ID to initial tube ID before expansion.

COMPARATIVE EXAMPLE

The comparative force necessary to advance a balloon made from copolymer II as compared to a balloon made from PET through a guide catheter was measured.

Two different types of tubing (0.021 inches I.D. × 0.031 inches O.D.) made from copolymer II and PET, respectively, were prestretched to a 2:1 ratio using 200 gm of tension at 93° C. and then formed into copolymer II and PET balloons using a 3.0 mm mold.

While vacuum was applied to the proximal end of the tubing, an 18 mil diameter mandrel was inserted at the distal end and extended through the balloon into the proximal waist. The distal end of the mandrel was allowed to extend about 7 mm past the open end of the distal waist and sealed off while under vacuum.

The balloon body was then flattened into a "winged" collapsed balloon under vacuum. A point medial to the vacuum connection and the balloon was sealed, leaving the winged structure.

A 5 mm section of an 8F guide catheter was mounted in a 37° C. bath with the soft tip pointing downwards.

A vertically translating stepped-motor driven stage was positioned above the guide catheter tip.

The copolymer II and PET balloons were pulled into the guide catheter tip, and the output recorded onto an XY recorder from a load sensor calibrated to a 100gm weight.

RESULTS

The copolymer II and the PET balloons both demonstrated twin peaks corresponding to the force needed to fold the balloon cones as it is drawn through a guide catheter. The first peak represents the force required to initiate folding in the proximal cone. This folding action includes a significant amount of the force required to retract the deflated balloon into a guide catheter. A second peak similarly represents the force required to initiate folding in the distal cone. The trough between the peaks is the force required to fold the body of the balloon along with the frictional force of the balloon surface against the surface of the guick catheter. The copolymer II balloon clearly required lower force to advance it past the guide catheter tip as illustrated by the data set forth in Table IV.

TABLE IV

| Balloon Material | Wall Thickness (inches) | 1st Peak (g) | 2nd Peak (g) | Trough (g) |
|---|---|---|---|---|
| Copolymer II | .00110 | 128.4 | 119.36 | 23.87 |
| PET | .00115 | 152.93 | 111.9 | 38.046 |

The different embodiments of the present invention as described herein are not intended to limit the scope of the following claims. Workers skilled in the art will readily appreciate that obvious change may be made in form and detail without departing from the spirit and scope of the present invention.

We claim:
1. A dilation catheter comprising:
    a compliant balloon having at least one layer of a thermoplastic material comprising a random copolymer consisting essentially of random repeating units of ethylene terephthalate and ethylene isophthalate.

2. A dilation catheter of claim 1 wherein said random copolymer has a ratio of ethylene terephthalate units to ethylene isophthalate units of between 99:1 to 80:20.

3. A dilatation catheter of claim 1 wherein said random copolymer has a ratio of ethylene terephthalate units to ethylene isophthalate units of between 95:5 to 90:10.

4. A dilatation catheter of claim 1 wherein said random copolymer has a ratio of ethylene terephthalate units to ethylene isophthalate units of 92:8.

5. A dilation catheter of claim 1 wherein said balloon has a radial expansion at 37° of greater than 3% at 200 psi and greater than 7% at burst.

6. A dilatation catheter of claim 1 wherein said balloon has a radial expansion at 37° of greater than 5% at 200 psi and greater than 10% at burst.

7. A dilation catheter of claim 1 wherein said balloon has a tensile strength of less than 40,000 psi.

8. A dilation catheter of claim 1 wherein said random copolymer has an intrinsic viscosity of less than 0.8 dl/g.

9. A dilation catheter of claim 1 wherein said balloon has a wall thickness between 0.0076–0.051 mm.

10. A dilatation catheter balloon comprising: at least one layer of a random copolymer of ethylene terephthalate and ethylene isophthalate having a wall thickness of between 0.0076–0.051 mm, a tensile strength less than 40,000 psi, an intrinsic viscosity less than 0.8 dl/g and a radial expansion of greater than 3% at 200 psi.

11. A dilatation catheter balloon of claim 10 wherein said random copolymer layer is compliant at 37° C.

12. A dilatation catheter balloon of claim 10 wherein said random copolymer layer is more amorphous and less crystalline than a biaxially oriented polyethylene terephthalate homopolymer balloon having a tensile strength greater than 31,000 psi.

13. A dilation catheter balloon having at least one layer of a thermoplastic material comprising a random copolymer having random repeating units of ethylene terephthalate and ethylene isophthalate.

14. A dilation catheter balloon of claim 13 wherein the random copolymer has an intrinsic viscosity of less than 0.8 dl/g.

15. A dilation catheter balloon of claim 13 wherein the balloon has a radial expansion at 37° C. of greater than 3% at 200 psi and greater than 7% at burst.

16. A dilation catheter balloon of claim 13 wherein the random copolymer has a ratio of ethylene terephthalate units to ethylene isophthalate units of between 99:1 and 80:20.

17. A dilation catheter balloon of claim 13 wherein the balloon has a wall thickness of between 0.0076 and 0.051 mm.

18. A dilation catheter balloon of claim 13 wherein the balloon is made of only one layer.

19. A dilation catheter balloon of claim 13 wherein the force required to initiate folding of the balloon to draw it through a guide catheter is less than the force required to fold a balloon of comparable wall thickness made from biaxially oriented polyethylene terephthalate.

20. A dilation catheter balloon of claim 13 wherein the random copolymer consists of random repeating units of ethylene terephthalate and ethylene isophthalate.

21. The dilatation catheter balloon of claim 13 wherein the random copolymer has a melting point of at least 221° C.

22. A method of making dilation catheter balloon comprising the steps of:
   a) providing tubing comprising a thermoplastic material comprising a random copolymer having random repeating units of ethylene terephthalate and ethylene isophthalate; and
   b) stretching and molding said tubing to form a dilation catheter balloon.

* * * * *